(12) United States Patent
Schwartz et al.

(10) Patent No.: US 7,351,869 B2
(45) Date of Patent: Apr. 1, 2008

(54) CRYSTALLIZATION METHOD FOR PURIFICATION OF CALCIPOTRIENE

(75) Inventors: Anchel Schwartz, Rehovot (IL); Asher Maimon, Petach Tiqva (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 601 days.

(21) Appl. No.: 10/717,148

(22) Filed: Nov. 18, 2003

(65) Prior Publication Data
US 2004/0138184 A1    Jul. 15, 2004

Related U.S. Application Data

(60) Provisional application No. 60/427,258, filed on Nov. 18, 2002.

(51) Int. Cl.
*C07C 35/08*    (2006.01)
(52) U.S. Cl. .................................................. 568/828
(58) Field of Classification Search .................. 568/828
See application file for complete search history.

(56) References Cited

U.S. PATENT DOCUMENTS

| | | | |
|---|---|---|---|
| 4,866,048 A | 9/1989 | Calverley et al. |
| 5,292,727 A | 3/1994 | Godtfredsen |
| 5,447,924 A | 9/1995 | Bretting |
| 5,716,945 A | 2/1998 | Grue-Sorensen |
| 5,763,426 A | 6/1998 | Hansen et al. |
| 5,824,313 A | 10/1998 | Daynes et al. |
| 5,994,332 A | 11/1999 | Calverley |
| 6,162,801 A | 12/2000 | Kita |
| 6,197,982 B1 | 3/2001 | Bretting |
| 6,231,875 B1 | 5/2001 | Sun et al. |
| 6,310,226 B1 | 10/2001 | Calverley et al. |
| 6,399,797 B1 | 6/2002 | von Daehne et al. |
| 2002/0004063 A1 | 1/2002 | Zhang |
| 2002/0022052 A1 | 2/2002 | Dransfield |
| 2002/0071852 A1 | 6/2002 | Deckers et al. |
| 2002/0106337 A1 | 8/2002 | Deckers et al. |
| 2003/0166226 A1* | 9/2003 | Shapiro et al. |

FOREIGN PATENT DOCUMENTS

| WO | WO-94/15912 | * | 7/1994 |
| WO | WO 03 060094 | | 7/2003 |

OTHER PUBLICATIONS

PCT International Search Report—PCT/US03/37138.
Martin J. Caverley, "Synthesis of MC 903, a biologically active vitamin D metabolite analogue", Tetrahedron, vol. 43, No. 20, 1987, pp. 4609-4616.
Caverley, M. J. and Bretting, C., "1-alpha-24S-dihydroxy-26, 27-cyclo-22-yne-vitamin D3: the side chain tirple bond analogue of MC 903 (calcipotriol)", Bioorganic and Medicinal Chemistry Letters, vol. 3, n. 9, 1993, pp. 1841-1844.

* cited by examiner

*Primary Examiner*—Shelley A. Dodson
(74) *Attorney, Agent, or Firm*—Kenyon & Kenyon LLP

(57) ABSTRACT

Provided is a crystallization method for reducing the level of impurities in calcipotriene in which a solution of a starting calcipotriene in a first process solvent, for example THF, is combined with second process solvent, for example methyl formate, and, after cooling, calcipotriene is isolated. The method can include a slurry step for reducing the level of residual first process solvent.

23 Claims, No Drawings

CRYSTALLIZATION METHOD FOR PURIFICATION OF CALCIPOTRIENE

RELATED APPLICATIONS

The present Application claims the benefit of U.S. Provisional Patent Application 60/427,258, filed Nov. 18, 2002.

FIELD OF THE INVENTION

The present invention relates to the purification of and particle size of calcipotriene.

BACKGROUND OF THE INVENTION

Calcipotriene, (5Z,7E,22E,24S)-24-cyclopropyl-9,10-secochola-5,7,10(19), 22-tetraene-1α,3β,24-triol, is a known antipsoriatic analog of vitamin D analog having structure I.

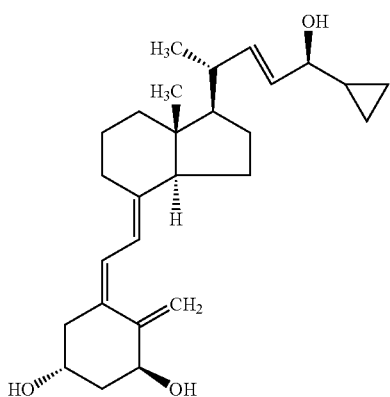

The synthesis of calcipotriene requires many synthetic steps in which undesired side products are obtained. Therefore, the final product can be contaminated not only with side product derived from the last synthetic step of the process but also with compounds that were formed in previous steps. These side products are usually excluded by purification methods such as chromatography, triturating, and crystallization. Purification by chromatography is a frequently used purification method. Because the unwanted products are often structural isomers of the desired final product, it is almost impossible to get the desired separation and, hence, purity of the drug.

Depending on the method used to synthesize calcipotriene, different minor unwanted compounds can accompany the final product. Thus, applying conditions developed by Barton and Hesse, *J. Org. Chem.* 51, 1637 (1987), C-1 hydroxylation is effected with selenium dioxide accompanied by N-methylmorpholin N-oxide as a reoxidant to give 1-α-hydroxylation and about 15% of 1-β hydroxylation, of which about 0.2-1% remains in the final product after chromatographic steps. One of the most unavoidable by-products obtain during thermal cheletropic extrusion of $SO_2$ is the C-20 epimer.

Vitamin D analogs like calcipotriene are known to be light-sensitive and this may lead to cis-trans isomerization at the 5,6 bond. Since vitamin D analogs like calcipotriene are heat sensitive, the appropriate solvent for purification is characterized by a low boiling point. According to the published literature, the most commonly used solvent is methyl formate (b.p. 32° C., threshold limit value 5000 ppm). Alcoholic solvents such as methanol, ethanol, and isopropanol (IPA) have not proved suitable because calcipotriene is highly soluble in these solvents. The reverse situation is encountered with highly apolar solvents (e.g. hydrocarbons) in which calcipotriene is essentially insoluble. Other solvents, which can be candidates for purification (e.g. recrystallization) are acetone, ethyl acetate, and mixtures of them. The drawback to these solvents is their high boiling points, which can translate to high residual solvent in the calcipotriene drug substance.

Since the solubility of calcipotriene in methyl formate is low, about 1g calcipotriene/150 mL of methyl formate, the crystallization of significant quantities of calcipotriene from methyl formate is performed using huge quantities of solvent. Moreover, to obtain reliable yield, one needs to concentrate the solution to about 1:90. This situation raises many technological and engineering problems. Recrystallization from methyl formate is also time consuming, increasing the chances that impurities will be formed.

Another important parameter influenced by the recrystallization process is the crystal size of the calcipotriene drug substance. The need to control the particle size distribution (PSD) can often pose a significant challenge in the crystallization process development. The PSD of an active pharmaceutical ingredient (API) has a dramatic impact on the formulation of drugs, especially for hydrophobic compounds, which have limited solubility in aqueous systems. When methyl formate is used for the recrystallization of calcipotriene, the particle size can arrive to 70 micron (μ), which is much bigger than the desired size. One can obtain smaller particle size by increasing stirring rate, but this approach usually leads to filtration problems, as the material stocked on the reactor. Consequently, much material is lost.

Clearly, there is a need for purification methods for calcipotriene that use much smaller volumes of solvent whilst achieving the desired purity and particle size.

Crystallization is known to be the simplest process that can be used for purification of organic compounds. Moreover, in the vitamin D family there are undesired compounds, which can be excluded only by crystallization. This is particularly true in the case of calcipotriene.

We have now found a crystallization process using a binary mixture of solvents to obtain pure calcipotriene with certain crystal size.

SUMMARY OF THE INVENTION

In one aspect, the present invention relates to a method of crystallizing calcipotriene including the steps of: providing a solution of a starting calcipotriene in a first solvent selected from: lower alkyl alcohols, especially isopropanol, lower aliphatic ketones, especially acetone, alkyl esters of lower carboxylic acids, and cyclic ethers, especially tetrahydrofuran; combining, with mechanical agitation, the provided solution with from about 1 to about 100 volumes, especially about 30 volumes, of a second solvent, especially methyl formate or hexane; cooling the combination to a temperature of less than about −10° C., especially at a cooling rate of about 40° C. per hour or less, and isolating calcipotriene from the resulting suspension, wherein when the first solvent is a cyclic ether the second solvent is especially methyl formate, when the first solvent is a lower alkyl alcohol the second solvent is especially a lower hydrocarbon, and when the first solvent is a lower dialkyl ketone, the second solvent is especially methyl formate.

In another aspect, the present invention relates to a method of making calcipotriene having a reduced level of impurities, and to the calcipotriene so obtained, including the steps of: providing a solution of a starting calcipotriene in a first solvent selected from: lower alkyl alcohols, especially isopropanol, lower aliphatic ketones, especially acetone, alkyl esters of lower carboxylic acids, and cyclic ethers, especially tetrahydrofuran; combining, with mechanical agitation, the provided solution with from about 1 to about 100 volumes, especially about 30 volumes, of a second solvent, especially methyl formate or hexane; cooling the combination to a temperature of less than about −10° C., especially at a cooling rate of about 40° C. per hour or less, and isolating calcipotriene from the resulting suspension, wherein when the first solvent is a cyclic ether the second solvent is especially methyl formate, when the first solvent is a lower alkyl alcohol the second solvent is especially a lower hydrocarbon, and when the first solvent is a lower dialkyl ketone, the second solvent is especially methyl formate.

In yet another aspect, the present invention relates to a method of making calcipotriene having a reduced level of impurities and reduced level of first process solvent, and to the calcipotriene so obtained, including the steps of: providing a solution of a starting calcipotriene in a first solvent selected from: lower alkyl alcohols, especially isopropanol, lower aliphatic ketones, especially acetone, alkyl esters of lower carboxylic acids, and cyclic ethers, especially tetrahydrofuran; combining, with mechanical agitation, the provided solution with from about 1 to about 100 volumes, especially about 30 volumes, of a second solvent, especially methyl formate or hexane; cooling the combination to a temperature of less than about −10° C., especially at a cooling rate of about 40° C. per hour or less, isolating calcipotriene from the resulting suspension; suspending the isolated calcipotriene in a suspending volume of suspending solvent, especially methyl formate, at about −10° C. to about 20° C. with controlled agitation for a suspension time, and isolating from the suspension so obtained calcipotriene having a reduced level of impurities and a reduced level of first process solvent. In particular aspect, when the first solvent is a cyclic ether the second solvent is especially methyl formate, when the first solvent is a lower alkyl alcohol the second solvent is especially a lower hydrocarbon, and when the first solvent is a lower dialkyl ketone, the second solvent is especially methyl formate.

In still a further aspect, the present invention relates to pharmaceutical compositions including at least one pharmaceutically acceptable excipient and calcipotriene obtained through any of the methods recited above.

DETAILED DESCRIPTION OF THE INVENTION

Crystallization is known to be a simple process that can be used for purification of organic compounds. Moreover, in the vitamin D family there are undesired compounds (impurities) that can be excluded only by crystallization. This is particularly true in the case of calcipotriene. The present invention provides, inter alia, a novel method of crystalization of calcipotriene.

As used herein, the terms "average" and "mean" are used interchangeably and, when used in reference to the size of calcipotriene crystals or particles, refer to the arithmetic mean of a statistically significant number of measurements. Average nominal particle size can be determined by well-known gas absorption techniques or measured by microscopic techniques using image analysis.

The particles or crystals of calcipotriene can be of any shape. Reference to nominal particle size in relation to crystals of calcipotriene, particularly when determined by microscopy, does not imply the size in any particular dimension or direction of any individual calcipotriene crystal in isolation. Rather, it refers to an average or mean of measurements on a statistically significant number of crystals, measured along dimensions or directions selected at random. Thus average nominal particle size refers to the arithmetic mean of measurements along randomly selected dimensions or directions on a statistically significant number of particles.

As used herein in connection with a measured quantity, the term about indicates that variation in the measured quantity as would be expected by the skilled artisan making the measurement or determination and exercising a level of care commensurate with the objective of the measurement and the precision of the measuring apparatus being used.

Calcipotriene having a reduced level (relative to the starting calcipotriene) of impurities has a relatively lower level of impurities, especially a reduced level of beta C3-OH, C21, C24-OH, and C5E isomers. Thus, calcipotriene having a reduced level of impurities refers to calcipotriene having a reduced level of impurities, especially beta C3-OH, C21, C24-OH, and C5E isomers, relative to the level of impurities in the starting calcipotriene. For purposes of the present invention, any residual first or second solvents (both are process solvents) in purified calcipotriene are not considered impurities. The level of impurities, in particular the level of beta C3-OH, C21, C24-OH, and C5E isomers in calcipotriene can be determined by high pressure liquid chromatography, also known as high performance liquid chromatography, and abbreviated HPLC, as described hereinbelow.

In one embodiment, the present invention provides a method of making calcipotriene having a reduced level of impurities including the steps of: providing a solution of a starting calcipotriene in a first solvent (first process solvent) at a concentration of between about 15% and about 25%, weight-to-volume, at an initial temperature of about 18° to about 30° C.; combining the provided solution with between about 1 and about 100, preferably between 1 and about 30, times its volume (i.e. 1-100 preferably 1-30 volumes) of second solvent (second process solvent); cooling the combination, with controlled agitation, to a temperature of about −15° C. or less, preferably at a cooling rate of less than about 40° C. per hour; and isolating calcipotriene having a reduced level of impurities relative to the starting calcipotriene. Calcipotriene so purified will typically have a nominal average particle size between about 15μ and about 40μ.

Calcipotriene from a variety of sources can be used as starting calcipotriene. Calcipotriene obtained from the practice of the methods disclosed in U.S. Provisional Patent Application 60/348,082, filed Jan. 10, 2002, and 60/388,520 filed Jun. 13, 2002 is suitable as starting calcipotriene. Calcipotriene as prepared by example 1 below is an example of a preferred starting calcipotriene.

First solvents (i.e. first process solvents) are characterized in part by their ability to form solutions of calcipotriene at about 25° C. having a concentration of at least about 20%, weight-to-volume. Preferred first solvents are capable of forming solutions of calcipotriene at about 25° C. having a concentration of at least about 25%, weight-to-volume, and have a boiling point at atmospheric pressure of less than about 90° C., more preferably less than about 80° C. First solvents can be further characterized by their ability to be combined with second solvents, discussed below, to form mixed solvents in which the solubility of calcipotriene is reduced relative to its solubility in first solvent alone.

Cyclic ethers are examples of first solvents that can be used in the practice of the present invention. The cyclic ethers can have one or two ether oxygen atoms and include oxacyclobutane, tetrahydrofuran, and 1,3-dioxolane. Tetrahydrofuran is a particularly preferred cyclic ether. The lower alkyl alcohols, acetone, and ethyl acetate are other examples of first solvents that can be used in the practice of the present invention. Lower alkyl alcohols useful in the practice of the present invention have the formula ROH wherein R is a linear or branched alkyl group having from 1 to 5 carbon atoms. iso-propanol (iso-propyl alcohol) is a preferred lower alkyl alcohol.

Lower alkyl ketones (dialkyl ketones) are also useful as first solvents in the practice of the present invention. Lower alkyl ketones have the formula R1-C(O)—R2, wherein R1 and R2 are the same or different and are linear or branched alkyl groups having 1-3 carbon atoms.

The second solvent (i.e. second process solvent) functions as an anti-solvent. An anti-solvent is a liquid, miscible with first solvent, that, when combined with a solution of calcipotriene in a first solvent, results in a solution of calcipotriene in mixed solvent wherein the solubility of calcipotriene in mixed solvent is reduced relative to its solubility in first solvent alone. Reduced solubility implies that, for a given quantity of calcipotriene, more of a solvent is required to effect dissolution or, for a given ratio of calcipotriene to solvent, the combination of calcipotriene and solvent must be heated to a higher temperature to effect dissolution of the calcipotriene, if complete dissolution can be effected at all.

Examples of second solvents include methyl formate and lower hydrocarbons.

Lower hydrocarbons useful in the practice of the present invention can be linear or branched and have the general formula $C_nH_{2n+2}$ wherein n is between 5 and 8. In a preferred embodiment, isopropanol is the first solvent and hexane is the second solvent.

In a particularly preferred embodiment, THF is the first solvent and methyl formate is the second solvent.

The kind and volume of second solvent are selected such that, when a given volume of a solution of calcipotriene in first solvent is combined at about 25° C. or higher with about 1 to about 30 times its volume (i.e. with 1-30 volumes) of second solvent, the solubility of calcipotriene is reduced so that, when the temperature of the resulting solution is reduced the calcipotriene begins to precipitate from the solution at a temperature between about 5° and 110° C.

In the practice of the present invention, a solution of calcipotriene in first solvent having a concentration of between about 15% and about 25%, weight-to-volume, is combined at about 25° C. or above, with agitation, with 1 to 100, preferably 1 to 30, times its volume of second solvent. The resulting solution is then cooled, with controlled agitation, to a temperature between about −10° C. and about −20° C., preferably between about −11° C. and about −18° C., at a cooling rate of less than about 40° C. per hour, preferably less than about 20° C. per hour, most preferably less than about 10° C. per hour.

When the purification method of the present invention is carried-out in laboratory-scale equipment, for example a flask with an overhead paddle-type stirrer, controlled agitation is stirring at about 210-350 RPM. The resulting purified calcipotriene typically has the desired nominal average particle size of about 15μ to about 40μ. The skilled artisan will know to optimize, by routine experimentation, the agitation speed according to the type and scale of equipment used to achieve a nominal average particle size of about 15μ to 40μ. The resulting suspension can be held at a temperature between about −10° C. and about −20° C. for a holding time. When a holding time is use, the preferred holding time is about 10 to about 24 hours. The desired particle size can, of course, be achieved using other methods of particle size reduction, for example milling.

Calcipotriene having a reduced level of impurities can be isolated from the suspension by any means known in the art, for example filtration (gravity or suction) or decanting, to mention just two. The isolated calcipotriene can be and preferably is dried at 25° to 40° C. Calcipotriene so isolated typically has a nominal average particle size of 15μ to 40μ and such calcipotriene is another embodiment of the present invention.

Calcipotriene having a reduced level of impurities can and typically does contain residual first process solvent. Residual process solvents can be quantified by application of known chromatographic or thermogravimetric techniques. The present invention also provides a method of reducing residual first process solvent.

In preferred embodiments, the isolated purified calcipotriene (i.e. calcipotriene having a reduced level of impurities) is treated by suspending it, with agitation, in a suspending solvent for a suspending time, whereby the level of residual first process solvent in the calcipotriene is reduced.

In such embodiments, the level of residual first solvent in purified calcipotriene obtained by the method of the present invention is reduced in a slurry process. In the slurry process, purified calcipotriene having a higher than desired level of residual first solvent is combined and agitated with methyl formate slurry solvent for a slurry time. A volume of about 5 to about 20 mL of methyl formate slurry solvent per gram of calcipotriene is typically sufficient. The slurry time can be from about 1 to about 5 hours. The skilled artisan will know to adjust the slurry time depending on, among other things, the amount of residual first solvent in the calcipotriene and the volume of methyl formate used. The skilled artisan will also know to use minimal the minimum practical agitation in the slurry step so as to avoid disrupting the PSD of the calcipotriene, unless such is desired In a preferred embodiment, the present invention provides crystallization process for calcipotriene employing a binary mixture of solvents to obtain calcipotriene having a reduced level of impurities and a certain crystal size. The most preferred binary mixture is THF and methyl formate in a ratio of about 1:50 especially about 1:30 (THF: methyl formate). Crude calcipotriene is dissolved in 4-6 volumes, (i.e. mL/g) of THF, then methyl formate is added. The clear solution is filtered to discard any undissolved materials. The solution is then cooled gradually (for about 1 to about 18 hours) between about −10° C. to about −18° C. while stirring at 210-350 rpm with mechanical stirrer or magnetic stirrer. After a period of time of between about 12 to about 24 hours the crystals are isolated by filtration and washed with methyl formate. The product can then be slurried in 5 to 20 volumes (mL/g) of methyl formate, stirring the suspension for 1 to 5 hours at −10° C. to 20° C. After filtration and washing the crystals with methyl formate, the product is dried in an oven for 20 to 48 hours at 2 to 40° C. The calcipotriene having a reduced level of impurities so obtained typically has a nominal average particle size of about 15μ to about 40μ.

One knowledgeable in the art of purification of calcipotriene will recognize that the volume of solvents used in the practice of the present invention is much less than the volume of solvents used in the practice of the methods of the prior art.

HPLC is well-known to those skilled in the art of pharmaceutical chemistry. The technique employs a column packed with a stationary phase, onto which a sample to be separated is loaded. The sample is then eluted with a suitable eluent. Elution can be isocratic or so-call solvent program, wherein the composition of the eluent is varied regularly (e.g. linearly) or irregularly (e.g. stepwise) over time. Pretreated silica gel, well known in the chromatographic arts, is a suitable stationary phase. Elution with 5% (v/v) ethyl acetate in hexane followed by neat ethyl acetate is but one example of an elution program that produces the desired separation. Others will be deduced by the skilled artisan through routine methods development.

Purified calcipotriene having a reduced level of impurities obtainable by the method of the present invention has less than about 0.1% each of C3-OH, C21, C24-OH, and C5 E isomers, where the percentages are area percentages of the respective peaks in the HPLC chromatogram.

In yet another embodiment, the present invention provides pharmaceutical compositions and dosage forms thereof that include calcipotriene purified by the method of the present invention. The dosage forms can be for oral administration, or they can be for topical administration.

In addition to the calcipotriene, the pharmaceutical compositions of the present invention can contain one or more excipients, such as diluents, binders, disintegrants, glidants, and lubricants.

Diluents increase the bulk of a solid pharmaceutical composition and can make a pharmaceutical dosage form containing the composition easier for the patient and caregiver to handle. Diluents for solid compositions include, for example, microcrystalline cellulose, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates, potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include acacia, alginic acid, carbomer, carboxymethylcellulose sodium, dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylates, povidone, pregelatinized starch, sodium alginate and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium, colloidal silicon dioxide, croscarmellose sodium, crospovidone, guar gum, magnesium aluminum silicate, methyl cellulose, microcrystalline cellulose, polacrilin potassium, powdered cellulose, pregelatinized starch, sodium alginate, sodium starch glycolate and starch.

Glidants can be added to improve the flow properties of non-compacted solid composition and improve the accuracy of dosing. Excipients that can function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product form the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Selection of excipients and the amounts to use can be readily determined by the formulation scientist based upon experience and standard procedures in the field.

In yet another embodiment, the present invention provides pharmaceutical compositions for topical administration, for example creams, ointments, and lotions.

Creams and ointments are semisolid pharmaceutical compositions intended for external topical administration. Creams, ointment, and lotions are formulated with a base that can be an oleaginous-type, an emulsion-type, or a water-soluble type. Petrolatum and hydrophilic petrolatum are examples of oleaginous bases. Lanolin is an example of a substance that can be used to form a water-in-oil emulsion-type base. Oil-in-water type emulsion bases (water removeable bases) can be formulated with, for example, petrolatum in combination with an alcohol such as cetyl or stearyl alcohol (internal oil phase), the remainder being water, emulsifier and, optionally, humectant.

Oleaginous bases typically are petrolatum or wax- or liquid parafin-modified petrolatum, but mineral oil gelled with addition of polyetheylene as is know in the art is also suitable as an oleaginous base. Hydrophilic petrolatum and lanolin are examples of an absorption base that can be used to make pharmaceutical compositions of the present invention. Bases of this type can form water-in-oil emulsions.

Water-removable, oil-in-water bases can also be used to make pharmaceutical compositions of the present invention. The oil phase can be, for example, petrolatum or liquid petroleum, with or without an alcohol such as cetyl alcohol or stearyl alcohol. Water removable bases are formulated with anionic, cationic, or nonionic emulsifiers as is known in the art.

Water soluble bases such as polyethylene glycol $<M>_n$ ~400 to 5000, can also be used as base in the practice of the present invention.

The pharmaceutical compositions of the present invention for topical administration can, if desired, contain an antimicrobal preservative such as sorbic acid, benzoic acid, formaldehyde, a halogenated phenol, or a quaternary ammonium compound.

Pharmaceutical compositions of the present invention for topical administration can be prepared by any of the methods known in the art, for example, levigation. The skilled artisan will know to select the methods based on the type of based used. Formulation and compounding of creams, ointments, and lotions is described in Lawrence H. Block, Ph.D., *Medicated Applications*, in, II Remington: THE SCIENCE AND PRACTICE OF PHARMACY 1577, 1585-91 (19*th* ed., Alfonso R. Gennaro, ed., 1995), incorporated herein by reference.

The present invention in certain of its embodiments is demonstrated in the following non-limiting examples.

EXAMPLE 1

Crystallization of Calcipotriene from Acetone

Calcipotriene (14.3 g) was dissolved in 280 ml of acetone. The clear solution was filtered through glass wool then concentrated by evaporation to 145 g. The solution was cooled to −18° C. over 2.5 hours then keeping this temperature for 16 hours stirring at 220 rpm. The crystals were filtered and washed with cold (−10° C.) 50 ml acetone then dried on an oven at 33° C. for 5 hours to give 10.4 g. Purity: 99.%.

EXAMPLE 2

Crystallization of Calcipotriene from Acetone

Calcipotriene (14.3 g) was dissolved in 280 ml of acetone. The clear solution was filtered through glass wool then concentrated by evaporation to 145 g. The solution was cooled to −18° C. over 2.5 hours then kept at this temperature for 16 hours, with stirring at 220 rpm. The crystals were filtered and washed with cold (−18° C.) 50 ml acetone then dried on an oven at 26±3° C. for 5 hours to give 10.4 g. Purity: 99.%.

EXAMPLE 3

Crystallization of Calcipotriene from Methyl Formate

Calcipotriene (3.93 g) was dissolved in 450 ml of freshly distilled methyl formate. The clear solution was filtered through glass wool then concentrated by evaporation to 310 g. The solution was cooled to −18° C. over 3.5 hours then keeping this temperature for 18 hours while stirring at 300 rpm. The crystals were filtered and washed with cold (−10° C.) 20 ml freshly distilled methyl formate then dried in an oven at 28° C. for 24 hours to give 3.14 g. Average particle size was 58 micron. Purity: 99.7%.

EXAMPLE 4

Crystallization of Calcipotriene from Methyl Formate

Calcipotriene (3.93 g) was dissolved in 450 ml of freshly distilled methyl formate. The clear solution was filtered through glass wool then concentrated by evaporation to 310 g. The solution was cooled to −18° C. over 3.5 hours then kept at this temperature for 18 hours while stirring at 300 rpm. The crystals were filtered and washed with cold (−18° C.) 20 ml freshly distilled methyl formate then dried in an oven at 28° C. for 24 hours to give 3.14 g. Average particle size was 58 micron. Purity: 99.7%

EXAMPLE 5

Crystallization of Calcipotriene form THF/Methyl Formate

Calcipotriene (22.45 g) was dissolved in 100 ml dry THF. The solution was filtered through a glass wool to a 3L-reactor equipped with mechanical stirrer and thermometers. The glass woll was washed with 10 ml dry THF and the washings combined with the filtrate. Under N₂ atmosphere, 673 ml of freshly distilled methyl formate was added and the clear solution stirred at 265 rpm. The solution was cooled to −18° C. over 3.5 hours then keeping this temperature for 18 hours. The crystals formed were filtered and washed with 220 ml freshly distilled methyl formate. The wet material was added to methyl formate and the suspension was stirred at 260 rpm at 0° C. for 1.5 hours. The suspension was filtered and washed with cold (−10° C.) methyl formate then dried on an oven at 28 for 24 to give 17 g product. Residual solvents in the product were 417 ppm THF and 837 ppm methyl formate. The average particle size was 29 micron and purity was 99.9% by HPLC.

EXAMPLE 6

Crystallization of Calcipotriene Form THF/Methyl Formate

Calcipotriene (22.45 g) was dissolved in 100 ml dry THF. The solution was filtered through a glass wool into a 3 L-reactor equipped with mechanical stirrer and thermometers. The glass woll was washed with 10 ml dry THF and the washings combined with the filtrate. Under N₂ atmosphere, 673 ml of freshly distilled methyl formate was added and the clear solution stirred at 265 rpm. The solution was cooled to −18° C. over 3.5 hours then keeping this temperature for 18 hours. The crystals formed were filtered and washed with 220 ml freshly distilled methyl formate. The wet material was added to methyl formate and the suspension was stirred at 260 rpm at 0° C. for 1.5 hours. The suspension was filtered and washed with cold (−18° C.) methyl formate then dried on an oven at 28 for 24 to give 17 g product. Residual solvents in the product were 417 ppm THF and 837 ppm methyl formate. The average particle size was 29 micron and purity was 99.9% by HPLC

EXAMPLE 7

Crystallization of Calcipotriene from Acetone/Methyl Formate

To 2.14 Calcipotriene were added 10 ml dry acetone, then 165 ml of freshly distilled methyl formate was added. The clear solution was filtered through glass wool and the solution was cooled to −18° C. over 2.5 hours then kept at this temperature for 15 hours while stirring at 240 rpm. The crystals were filtered and washed with 21 ml cold (−10° C.) freshly distilled methyl formate then dried on an oven at 28° C. for 24 hours to give 1.63 g product. Purity: 99.6%.

What is claimed is:

1. A method of crystallizing calcipotriene comprising the steps of:
    a) providing a solution of a starting calcipotriene in a first solvent selected from: lower alkyl alcohols, lower aliphatic ketones, alkyl esters of lower carboxylic acids, and cyclic ethers,
    b) combining, with agitation, the provided solution with from about 1 to about 100 volumes of a second solvent,
    c) cooling the combination to a temperature of less than about −10° C., and
    d) isolating calcipotriene from the resulting suspension, wherein when the first solvent is a cyclic ether the second solvent is methyl formate, when the first solvent is a lower alkyl alcohol the second solvent is a lower hydrocarbon, and when the first solvent is a lower dialkyl ketone, the second solvent is methyl formate.

2. The method of claim 1 wherein the provided solution is combined with about 30 volumes of second solvent.

3. The method of claim 1 wherein the agitation is stirring at 210 to 260 RPM.

4. The method of claim 1 wherein the first solvent is a cyclic ether and the second solvent is methyl formate.

5. The method of claim 4 wherein the cyclic ether is tetrahydrofuran.

6. The method of claim 1 wherein the first solvent is iso-propyl alcohol and the second solvent is hexane.

7. The method of claim 1 wherein the first solvent is acetone and the second solvent is methyl formate.

8. The method of claim 1 wherein the combination is cooled at a cooling rate of less than about 40° C. per hour.

9. A method of making calcipotriene having a reduced level of impurities comprising the steps of:
 a) providing a solution of starting calcipotriene in a first solvent selected from: lower alkyl alcohols, lower aliphatic ketones, alkyl esters of lower carboxylic acids, and cyclic ethers,
 b) combining the provided solution, with agitation, with from about 1 to about 100 volumes of a second solvent,
 c) cooling the combination to a temperature of less than about −10° C. at a cooling rate between about 10° and about 40° C. per hour, and
 d) isolating from the resulting suspension calcipotriene having a reduced level of impurities, wherein when the first solvent is a cyclic ether the second solvent is methyl formate, when the first solvent is a lower alkyl alcohol the second solvent is a lower hydrocarbon, and when the first solvent is a lower dialky ketone, the second solvent is methyl formate.

10. The method of claim 9 wherein the agitation is stirring at about 210 to about 260 RPM.

11. The method of claim 9 wherein the provided solution is combined with about 30 volumes of second solvent.

12. The method of claim 9 wherein the first solvent is tetrahydrofuran and the second solvent is methyl formate.

13. The method of claim 9 wherein the first solvent is iso-propanol and the second solvent is hexane.

14. The method of claim 9 wherein the first solvent is acetone and the second solvent is methyl formate.

15. The method of claim 9 wherein the calcipotriene having a reduced level of impurities has an average nominal particle size of about 15µ to about 40µ.

16. A method of making purified calcipotriene having a reduced level of impurities and a reduced level of residual first process solvent comprising the steps of:
 a) providing a solution of starting calcipotriene in a first solvent selected from: lower alkyl alcohols, lower aliphatic ketones, alkyl esters of lower carboxylic acids, and cyclic ethers,
 b) combining the provided solution, with agitation, with from about 1 to about 100 volumes of a second solvent,
 c) cooling the combination to a temperature of less than about −10° C. at a cooling rate between about 10° and about 40° C. per hour,
 d) isolating from the resulting suspension calcipotriene having a reduced level of impurities, wherein when the first solvent is a cyclic ether the second solvent is methyl formate, when the first solvent is a lower alkyl alcohol the second solvent is a lower hydrocarbon, and when the first solvent is a lower dialkyl ketone, the second solvent is methyl formate,
 e) suspending the isolated calcipotriene in a suspending volume of methyl formate at a temperature between about −10° and about 20° C. with agitation for a suspension time, and
 f) isolating from the suspension purified calcipotriene having a reduced level of impurities and a reduced level of first process solvent.

17. The method of claim 16 wherein the calcipotriene having a reduced level of impurities and reduced level of first process solvent has a nominal average particle size of about 15µ to about 40µ.

18. The method of claim 16 wherein the agitation is stirring at about 210 to about 260 RPM.

19. The method of claim 16 wherein the provided solution is combined with about 30 volumes of second solvent.

20. The method of claim 16 wherein the suspension time is between about 1 and about 5 hours.

21. The method of claim 16 wherein the first solvent is tetrahydrofuran and the second solvent is methyl formate.

22. The method of claim 16 wherein the first solvent is iso-propanol and the second solvent is hexane.

23. The method of claim 16 wherein the first solvent is acetone and the second solvent is methyl formate.

* * * * *